US009522111B2

(12) United States Patent
Szewczyk et al.

(10) Patent No.: US 9,522,111 B2
(45) Date of Patent: Dec. 20, 2016

(54) COLOR CHANGING COMPOSITIONS

(75) Inventors: Gregory Szewczyk, Flemington, NJ (US); Neeta Atul Patel, Monmouth Junction, NJ (US); Suzanne Jogun, Wayne, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/365,082

(22) PCT Filed: Dec. 16, 2011

(86) PCT No.: PCT/US2011/065310
§ 371 (c)(1),
(2), (4) Date: Jun. 12, 2014

(87) PCT Pub. No.: WO2013/089761
PCT Pub. Date: Jun. 20, 2013

(65) Prior Publication Data
US 2015/0086486 A1  Mar. 26, 2015

(51) Int. Cl.
*A61K 8/73* (2006.01)
*A61Q 11/00* (2006.01)
*A61K 8/72* (2006.01)
*A61K 8/21* (2006.01)
*A61K 8/34* (2006.01)
*A61Q 17/00* (2006.01)
*A61K 8/81* (2006.01)
*A61K 8/02* (2006.01)
*A61K 8/46* (2006.01)
*A61K 8/49* (2006.01)

(52) U.S. Cl.
CPC ............ *A61K 8/731* (2013.01); *A61K 8/0216* (2013.01); *A61K 8/345* (2013.01); *A61K 8/347* (2013.01); *A61K 8/463* (2013.01); *A61K 8/4973* (2013.01); *A61K 8/8164* (2013.01); *A61Q 11/00* (2013.01); *A61Q 17/005* (2013.01); *A61K 2800/43* (2013.01); *A61K 2800/5424* (2013.01)

(58) Field of Classification Search
USPC .................................................. 424/49, 401
See application file for complete search history.

(56) References Cited

U.S. PATENT DOCUMENTS

| 3,535,421 | A | 10/1970 | Briner et al. |
|---|---|---|---|
| 3,538,230 | A | 11/1970 | Pader et al. |
| 3,662,059 | A | 5/1972 | Wiesner et al. |
| 3,678,154 | A | 7/1972 | Widder et al. |
| 3,696,191 | A | 10/1972 | Weeks |
| 3,862,307 | A | 1/1975 | Di Giulio |
| 3,937,807 | A | 2/1976 | Haefele |
| 3,959,458 | A | 5/1976 | Agricola et al. |
| 3,991,177 | A | 11/1976 | Vidra et al. |
| 4,051,234 | A | 9/1977 | Gieske et al. |
| 4,058,595 | A | 11/1977 | Colodney |
| 4,154,815 | A | 5/1979 | Pader |
| 4,340,583 | A | 7/1982 | Wason |
| 4,355,022 | A | 10/1982 | Rabussay |
| 4,842,847 | A | 6/1989 | Amjad |
| 4,866,161 | A | 9/1989 | Sikes et al. |
| 4,885,155 | A | 12/1989 | Parran et al. |
| 4,992,420 | A | 2/1991 | Neeser |
| 5,000,939 | A | 3/1991 | Dring et al. |
| 5,004,597 | A | 4/1991 | Majeti et al. |
| 5,275,805 | A | 1/1994 | Nabi et al. |
| 6,136,297 | A | 10/2000 | Sagel et al. |
| 6,419,902 | B1 | 7/2002 | Wright |
| 6,419,903 | B1 | 7/2002 | Xu et al. |
| 6,479,036 | B1 | 11/2002 | Stanier et al. |
| 6,669,929 | B1 | 12/2003 | Boyd et al. |
| 7,135,163 | B2 | 11/2006 | Winston et al. |
| 7,763,235 | B2 | 7/2010 | Boyd et al. |
| 8,647,648 | B2 | 2/2014 | Boyd et al. |
| 2002/0034479 | A1 | 3/2002 | Green |
| 2004/0247646 | A1 | 12/2004 | Ivory et al. |
| 2005/0019273 | A1 | 1/2005 | Boyd et al. |
| 2005/0031553 | A1 | 2/2005 | Mori et al. |
| 2005/0112189 | A1 | 5/2005 | Motoune et al. |
| 2005/0271601 | A1 | 12/2005 | Milanovich et al. |
| 2006/0134020 | A1 | 6/2006 | Robinson et al. |
| 2007/0020201 | A1 | 1/2007 | Boyd et al. |
| 2007/0148213 | A1 | 6/2007 | Ibrahim et al. |

(Continued)

FOREIGN PATENT DOCUMENTS

| EP | 0158189 | 6/1989 |
|---|---|---|
| EP | 0304789 | 3/1993 |
| EP | 0704561 | 4/1998 |
| EP | 2105122 | 9/2012 |
| FR | 2591102 | 6/1987 |
| JP | S60016913 | 7/1983 |
| JP | S63250314 | 10/1988 |
| JP | H09143027 | 6/1997 |
| JP | H09175970 | 7/1997 |
| JP | H10263057 | 10/1998 |

(Continued)

OTHER PUBLICATIONS

International Search Report and the Written Opinion issued in International Application PCT/US2011/65310 mailed Oct. 1, 2012. WO.

(Continued)

*Primary Examiner* — Lezah Roberts

(57) ABSTRACT

Described herein are oral care compositions comprising an antibacterial agent and a dissolvable film comprising a pigment which provide a color change signal after a sufficient period of brushing, wherein the dentifrice base has water activity less than 0.78 and comprises anionic polymer in free or salt form 10-25% by weight of the dentifrice base, and anionic surfactant less than 3% by weight; together with methods of making and using the compositions.

9 Claims, No Drawings

(56) References Cited

U.S. PATENT DOCUMENTS

| | | | |
|---|---|---|---|
| 2008/0014224 A1* | 1/2008 | Boyd | A61K 8/0208 424/401 |
| 2008/0063615 A1 | 3/2008 | MacDonald et al. | |
| 2008/0138369 A1 | 6/2008 | Boyd et al. | |
| 2008/0187497 A1 | 8/2008 | Agarwal et al. | |
| 2008/0187498 A1 | 8/2008 | Francis | |
| 2008/0245678 A1 | 10/2008 | Gantenberg | |
| 2008/0247967 A1 | 10/2008 | Sagel et al. | |
| 2008/0247968 A1 | 10/2008 | Sagel | |
| 2008/0247969 A1 | 10/2008 | Glandorf | |
| 2008/0247970 A1 | 10/2008 | Gantenberg | |
| 2008/0248072 A1 | 10/2008 | Glandorf | |
| 2008/0248073 A1 | 10/2008 | Gantenberg | |
| 2009/0060597 A1 | 3/2009 | Yoshida et al. | |
| 2012/0070478 A1 | 3/2012 | Boyd et al. | |
| 2014/0161735 A1 | 6/2014 | Boyd et al. | |

FOREIGN PATENT DOCUMENTS

| | | |
|---|---|---|
| JP | 2001302474 | 10/2001 |
| JP | 2002316920 | 10/2002 |
| JP | 2004284956 | 10/2004 |
| JP | 2005075756 | 3/2005 |
| WO | WO2010114551 | 10/2010 |

OTHER PUBLICATIONS

Written Opinion of the International Preliminary Examining Authority issued in International Application PCT/US2011/65310 mailed Jan. 23, 2014. WO.

* cited by examiner

COLOR CHANGING COMPOSITIONS

CROSS-REFERENCE TO RELATED PATENT APPLICATIONS

The present application is a U.S. national stage entry under 35 U.S.C. §371 of Patent Cooperation Treaty Patent Application No. PCT/US2011/65310, filed Dec. 16, 2011, the entirety of which is incorporated herein by reference.

BACKGROUND

It is recommended that children should brush their teeth for at least 45-60 seconds, and adults for at least 90 to 120 seconds. Most people, especially children, do not brush their teeth for a sufficient period of time to obtain maximum benefit, and moreover have difficulty accurately estimating the time necessary to brush the teeth.

There is a need for improved, consumer-friendly products and methods to encourage users to brush their teeth for a longer period of time.

SUMMARY

The present inventors have discovered that the timing of the color change can be adjusted through the film (composition & thickness) to occur at a specified time so as to provide a visual signal to the consumer that enough time has been spent brushing. One challenge faced, however, is how to stabilize the films so that they do not dissolve in the dentifrice yet dissolve when exposed to water and brushing action. In a typical dentifrice, the films break down within 2-4 days leaving the pigment to bleed within the dentifrice. Toothpaste formulas having water activity above 0.78 show significant film instability upon aging. However, compositions having water activity below 0.78 are stable over two months. Using a design of experiments approach, various factors are evaluated for their impact on film stability. Higher levels of anionic polymer in the formulation enhance stability. Anionic surfactant such as sodium lauryl sulfate, on the other hand, can have an unexpected detrimental affect on stability, and levels must be controlled to ensure acceptable stability.

The invention provides optimized dentifrice compositions comprising a dentifrice base and dissolvable films which provide a color change signal after a sufficient period of brushing, wherein the dentifrice base has water activity less than 0.78 and comprises anionic polymer salt 10-25% by weight of the dentifrice base, e.g. 10-20%, and anionic surfactant less than 3% by weight, e.g., 1-2%. The invention further provides methods of making and using the compositions.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention thus provides, in a first embodiment, a dentifrice composition (Composition 1) comprising a dentifrice base and dissolvable films comprising pigment which provides a color change signal after a sufficient period of brushing, wherein the dentifrice base has water activity less than 0.78 and comprises anionic polymer in free or salt form 10-25% by weight of the dentifrice base, e.g., 10-20%, and anionic surfactant less than 3% by weight, e.g., 1-2%. For example, 1.1. Composition 1 wherein the anionic polymer is an anionic polymeric polycarboxylate, e.g., 1:4 to 4:1 copolymers of maleic anhydride or acid with another polymerizable ethylenically unsaturated monomer, for example methyl vinyl ether/maleic anhydride having a molecular weight (M.W.) of about 30,000 to about 1,000,000, e.g. about 30,000 to about 800,000, optionally partially or fully in the form of an orally acceptable base addition salt, e.g., sodium, potassium or ammonium salt form.

1.2. Composition 1 further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;

1.3. Any of the foregoing compositions wherein a 1"×1" swatch of the film placed in water will not disintegrate and release active in water at room temperature in less than 5 minutes in the absence of agitation;

1.4. Any of the foregoing compositions wherein the dissolvable film comprises cellulose ethers, e.g., selected from
  (i) alkylcellulose, e.g., methylcellulose;
  (ii) hydroxyalkyl cellulose, e.g., selected from hydroxypropyl methyl cellulose, hydroxyethylpropyl cellulose, hydroxybutyl methyl cellulose, hydroxy propyl methyl cellulose, carboxymethyl cellulose and mixtures thereof;
  and (iii) mixtures thereof;

1.5. Any of the foregoing compositions wherein the dissolvable film comprises a starch, e.g. a pregelatinized starch;

1.6. Any of the foregoing compositions wherein the dissolvable film comprises a plasticizer, e.g., a polyalcohol, e.g., sorbitol, propylene glycol, glycerol, or low molecular weight polyethylene glycol, e.g., PEG 200;

1.7. Any of the foregoing compositions wherein the dissolvable film comprises propylene glycol, e.g., in an amount effective to provide plasticity to the film, e.g., about 20-30% by dry weight of the film;

1.8. Any of the foregoing compositions wherein the dissolvable film comprises a non-ionic surfactant or emulsifier, e.g., a polysorbate, e.g., polysorbate 80 (also known as polyoxyethylene(20) sorbitan monooleate, available commercially e.g., as Tween® 80), e.g., in an amount of about 1-5% by dry weight of the film;

1.9. Any of the foregoing compositions wherein the dissolvable film comprises a pigment; e.g., a red pigment, for example D&C Red 30, a green pigment, for example Pigment Green 7, a blue pigment, for example a phthalocyanine, for example Pigment Blue 15, or a combination of any of these pigments;

1.10. Any of the foregoing compositions wherein the dissolvable film is substantially dissolved after a period of greater than 30 seconds and less than 180 seconds of brushing, scrubbing or agitation in the presence of water;

1.11. Any of the foregoing compositions wherein the average thickness of dissolvable film is 1-4 mil, e.g. 1.5-3 mil, e.g. about 1.5 mil or about 3 mil;

1.12. Any of the foregoing compositions wherein the dissolvable film comprises, by dry weight of the film, 20-60% cellulose ethers selected from methyl cellulose, hydroxypropylmethyl cellulose, and mixtures thereof; 10-30% propylene glycol; 1-5% polysorbate 80; and 15-55% pigment;

1.13. Any of the foregoing compositions wherein the dissolvable film is in the form of film fragments, e.g., regular or irregular shapes or flakes;

1.14. Any of the foregoing compositions wherein the dentifrice base is a clear gel;

1.15. Any of the foregoing compositions comprising 1-arginine in free or orally acceptable salt form;

1.16. Any of the foregoing compositions comprising buffering agents, e.g., sodium phosphate buffer (e.g., sodium phosphate monobasic and disodium phosphate)

1.17. Any of the foregoing compositions comprising a humectant, e.g., selected from glycerin, sorbitol, propylene glycol, polyethylene glycol, xylitol, and mixtures thereof, e.g. 40-70%, e.g., 45-65%;

1.18. Any of the preceding compositions further comprising an abrasive or particulate;

1.19. The immediately preceding composition wherein the adhesive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof;

1.20. Any of the preceding compositions comprising an abrasive in an amount of about 15 wt. % to about 70 wt. % of the total composition weight;

1.21. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof;

1.22. Any of the preceding compositions further comprising at least one polymer in addition to the anionic polymer, e.g., selected from polyethylene glycols, polysaccharides (e.g., cellulose derivatives, for example carboxymethyl cellulose, or polysaccharide gums, for example xanthan gum or carrageenan gum), and combinations thereof;

1.23. Any of the preceding compositions further comprising flavoring, fragrance and/or coloring;

1.24. Any of the foregoing compositions comprising one or more antibacterial agents for example comprising an antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;

1.25. Any of the preceding compositions further comprising a whitening agent, e.g., a selected from the group consisting of peroxides, metal chlorites, perborates, percarbonates, peroxyacids, hypochlorites, and combinations thereof;

1.26. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.27. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate;

1.28. Any of the preceding compositions further comprising a soluble calcium salt, e.g., selected from calcium sulfate, calcium chloride, calcium nitrate, calcium acetate, calcium lactate, and combinations thereof;

1.29. Any of the preceding compositions further comprising a physiologically acceptable potassium salt, e.g., potassium nitrate or potassium chloride, in an amount effective to reduce dentinal sensitivity;

1.30. Any of the preceding compositions further comprising a breath freshener, fragrance or flavoring;

1.31. Any of the preceding compositions effective upon application to the oral cavity, e.g., with brushing, to (i) inhibit microbial biofilm formation in the oral cavity, (ii) to reduce plaque accumulation, (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues;

1.32. A composition obtained or obtainable by combining the ingredients as set forth in any of the preceding compositions;

1.33. Any of the preceding compositions further comprising effective amounts of additional agents selected from fluoride, 1-arginine in free or orally acceptable salt form, antibacterial agents, anti-inflammatory compounds, and whitening agents;

1.34. Any of the preceding compositions further comprising one or more of one or more of water, abrasives, surfactants, foaming agents, vitamins, polymers, enzymes, humectants, thickeners, antimicrobial agents, preservatives, flavorings, colorings and/or combinations thereof;

1.35. Any of the preceding compositions wherein the dentifrice base comprises the following ingredients (weight percent):

| Ingredients | Wt percent |
| --- | --- |
| WATER | 1-10 |
| FLUORIDE ION SOURCE, e.g., sodium fluoride | 0.1-0.5 |
| SWEETENER, e.g. sodium saccharin | 0-1 |
| HUMECTANT, e.g., glycerin, propylene glycol, sorbitol, or mixtures thereof | 50-60 |
| THICKENERS, e.g., sodium carboxymethyl cellulose, iota carrageenan, or mixtures thereof | 0-3 |
| ANIONIC COPOLYMER, e.g., methyl vinyl ether/maleic anhydride co-polymer | 10-20 |
| BASE to form salt with anionic co-polymer, e.g., NaOH, 50% solution | 0.5-2% |
| COLORING, e.g, titanium dioxide | 0-0.75 |
| ABRASIVE, e.g., Silica abrasive | 15-25 |
| ANIONIC SURFACTANT, e.g. sodium lauryl sulfate | 1-2 |
| ANTIBACTERIAL, e.g., triclosan | 0.1-1 |
| FLAVOR | 0-3 |

In some embodiments, substantially all of the pigment is released at one time. As used herein, the term "substantially all" refers to greater than 90% of the total amount of pigment contained in the film. In some embodiments, the film releases at least 90% of the total amount of pigment contained therein, at a particular point in time. In some embodiments, the film releases greater than 90% of the total amount of pigment contained therein, at a designated point in time. In some embodiments, the film releases at least 91% of the total amount of pigment contained therein, at the designated point in time. In some embodiments, the film releases at least 95% of the total amount of pigment contained therein, at the designated point in time. In some embodiments, the first releases at least 96% of the total amount of pigment contained therein, at the designated point in time. In some embodiments, the film releases at least 97% of the total amount of pigment contained therein, at the designated point in time. In some embodiments, the film releases at least 98% of the total amount of pigment contained therein, at the designated point in time. In some embodiments, the film releases at least 99% of the total amount of pigment contained therein, at the designated point in time.

The invention further provides methods to (i) inhibit microbial biofilm formation in the oral cavity, (ii) to reduce plaque accumulation, (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues; comprising applying to the oral cavity an effective amount of any of Composition 1, et seq.

The invention further provides a method of cleaning the teeth comprising brushing with a dentifrice according to Composition 1, et seq., wherein brushing is continued until the film disintegrates and the pigment provides a color signal to the user of adequate brushing, for example, wherein the brushing time before the film matrix dissolves is between 30 and 180 seconds, e.g., about 45-60 seconds for a toothpaste for use by a child and about 90-120 seconds for a toothpaste for use by an adult.

Orally Acceptable: The compositions of the invention are intended for topical use in the mouth, thus components for use in the present invention should be orally acceptable, that is, safe for topical use in the mouth, in the amounts and concentrations provided.

Salt Forms: The compositions of the invention are intended for topical use in the mouth, thus salts for use in the present invention should be orally acceptable, that is, safe for topical use in the mouth, in the amounts and concentrations provided. Suitable salts include salts known in the art to be pharmaceutically acceptable salts, which are generally considered to be orally acceptable for this purpose in the amounts and concentrations provided.

Water Activity: Water activity or $a_w$ correlates to the association between various non-aqueous constituents and solids, and is a measure of the energy status of the water in a system. It is defined as the vapor pressure of a liquid divided by that of pure water at the same temperature; therefore, pure distilled water has a water activity of exactly one. Thus total water content is related to water activity, but is also influenced by the presence of compounds such as humectants that interact strongly with water and reduce the vapor pressure of the composition.

Active Agents: The effective concentration of the active ingredients used herein will depend on the particular agent and the delivery system used, and whether the formulation is intended for general consumer use or use by dentists. The concentration will also depend on the exact form of active selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt %(expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product. Levels of antibacterial agents will vary similarly. For example, a triclosan toothpaste may contain about 0.3 wt % triclosan.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al.

and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Abrasives: The compositions of the invention, e.g. Composition 1 et seq. may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

Agents to Increase the Amount of Foaming: The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants: The compositions useful in the invention may contain anionic surfactants, for example i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents: The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

Polymers: The oral care compositions of the invention also optionally include one or more polymers in addition to the anionic polymer, such as polyethylene glycols, polysaccharides (e.g., cellulose derivatives, for example carboxymethyl cellulose, or polysaccharide gums, for example xanthan gum or carrageenan gum).

Anionic polymers include polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. Other useful anionic polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Enzymes: The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000, 939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes about 0.002% to about 2.0% in one embodiment or about 0.05% to about 1.5% in another embodiment or in yet another embodiment about 0.1% to about 0.5%.

Water: Water may also be present in the oral compositions of the invention. Water, employed in the preparation of commercial oral compositions should be deionized and free of organic impurities. The amount of water should be low enough so as not to provide a water activity greater than the limits described above.

Humectants: Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Other Optional Ingredients: In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional anti-plaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLE

Example 1

A prototype film is developed by encapsulating a pigment into a dissolvable polymer film. During brushing, the films swell from water and disintegrate, releasing the pigment and, thus, color change occurs to indicate the consumer when the brushing is done. One use for this film is for incorporation into a clear gel toothpaste providing a color change signal to the consumer after a predetermined brushing time, e.g., 45-60 sec for children and 90-120 sec for the adults.

The ingredients for the prototype film are set forth in Table 1:

TABLE 1

|  | Weight % of solids |
| --- | --- |
| Water |  |
| Hydroxypropylmethyl cellulose | 48.2 |
| Pigment | 30 |
| Propylene Glycol | 18 |
| Polysorbate (Tween 80) | 3.8 |
| Total Amount | 100.000 |

The film is then tested for stability in various toothpaste gel formulations with different levels of excipients.

In a typical dentifrice, the films break down within 2-4 days leaving the pigment to bleed within the dentifrice. It is unexpectedly found that toothpaste formulas having water activity of 0.78 or higher showed significant film instability upon aging, while those with lower water activity were stable over at least two months.

Various other factors are evaluated for their impact on film stability. Stability is surprisingly increased when levels of anionic polymer (Gantrez®) are increased to levels substantially higher than usual. Anionic surfactant (sodium lauryl sulfate) is demonstrated to have an unexpected detrimental affect on stability, although acceptable stability still can exist.

Examples of stable and unstable dentifrice formulations are shown in Table 2 (amounts given as weight percent of composition).

TABLE 2

| Ingredients | Unstable | Unstable | Unstable | Stable | Stable |
| --- | --- | --- | --- | --- | --- |
| WATER | 30 | 20.5 | 30 | 11.5 | 3 |
| SODIUM FLUORIDE | 0.24 | 0.24 | 0.24 | 0.24 | 0.24 |
| SODIUM SACCHARIN | 0.30 | 0.30 | 0.30 | 0.30 | 0.30 |
| GLYCERIN | 32 | 25.5 | 25 | 35 | 35 |
| SODIUM CMC | 1.10 | 1.10 | 1.10 | 1.10 | 1.10 |
| IOTA CARRA-GEENAN | 0.50 | 0.50 | 0.50 | 0.50 | 0.50 |
| SORBITOL | 10 | 10 | 9 | 10 | 18 |
| PROPYLENE GLYCOL | 0.50 | 0.50 | 0.50 | 0.50 | 0.50 |
| GANTREZ | 0 | 15.00 | 7.5 | 15.00 | 15.00 |
| NaOH, 50% SOLU | 0 | 1.20 | 0.6 | 1.20 | 1.20 |
| Titanium Dioxide | 0.75 | 0.75 | 0.75 | 0.75 | 0.75 |
| Silica | 21.5 | 21.5 | 21.5 | 21.5 | 21.5 |
| SLS | 1.50 | 1.50 | 1.50 | 1.0 | 1.50 |
| Films | 0.30 | 0.30 | 0.30 | 0.30 | 0.30 |
| TRICLOSAN | 0.30 | 0.30 | 0.30 | 0.30 | 0.30 |
| Flavor | 1.00 | 1.00 | 1.00 | 1.00 | 1.00 |
| Water activity (Aw) | 0.78 | 0.83 | 0.92 | 0.73 | 0.65 |

The invention claimed is:

1. An oral care composition comprising a dentifrice base; an antibacterial agent; and a dissolvable film comprising a pigment which provides a color change signal after a sufficient period of brushing, wherein the dentifrice base has a water activity less than 0.78 and comprises an anionic polymer in free or salt form in the amount of 10-25% by weight of the dentifrice base, and an anionic surfactant at an amount of less than 3% by weight;
wherein the dissolvable film comprises, by dry weight of the film, 20-60% cellulose ethers selected from methyl cellulose, hydroxypropylmethyl cellulose, and mixtures thereof; 10-30% propylene glycol; 1-5% polysorbate 80; and 15-55% pigment.

2. The composition according to claim 1 wherein the anionic polymer is methyl vinyl ether/maleic anhydride co-polymer having a molecular weight (M.W.) of about 30,000 to about 1,000,000, optionally partially or fully in the form of an orally acceptable base addition salt.

3. The composition according to claim 1 further comprising an effective amount of fluoride.

4. The composition according to claim 1 wherein a 1"×1" swatch of the film placed in water will not disintegrate and release active in water at room temperature in less than 5 minutes in the absence of agitation.

5. The composition according to claim 1 wherein the dissolvable film further comprises a starch.

6. The composition according to claim 1 wherein the dissolvable film is substantially dissolved after a period of greater than 30 seconds and less than 180 seconds of brushing, scrubbing or agitation in the presence of water.

7. The composition according to claim 1 further comprising a humectant selected from: glycerin, sorbitol, polyethylene glycol, xylitol, and a combination of two or more thereof.

8. The composition according to claim 1 further comprising an abrasive.

9. A method of cleaning the teeth comprising brushing with a composition according to claim 1, wherein brushing is continued until the film disintegrates and the pigment provides a color signal to the user of adequate brushing.

\* \* \* \* \*